United States Patent
Aoki et al.

(10) Patent No.: US 9,879,314 B2
(45) Date of Patent: Jan. 30, 2018

(54) **METHOD FOR DETECTING HLA-A*31:01 ALLELE**

(71) Applicant: RIKEN, Saitama (JP)

(72) Inventors: Masayuki Aoki, Kanagawa (JP); Michiaki Kubo, Kanagawa (JP); Naoya Hosono, Kanagawa (JP)

(73) Assignee: RIKEN, Saitama (JP)

( * ) Notice: Subject to any disclaimer, the term of this patent is extended or adjusted under 35 U.S.C. 154(b) by 489 days.

(21) Appl. No.: 14/381,678

(22) PCT Filed: Feb. 28, 2013

(86) PCT No.: PCT/JP2013/055285
§ 371 (c)(1),
(2) Date: Aug. 28, 2014

(87) PCT Pub. No.: WO2013/129542
PCT Pub. Date: Sep. 6, 2013

(65) Prior Publication Data
US 2015/0072874 A1   Mar. 12, 2015

(30) Foreign Application Priority Data
Feb. 29, 2012   (JP) .................... 2012-044752

(51) Int. Cl.
*C12Q 1/68*   (2006.01)
(52) U.S. Cl.
CPC ......... *C12Q 1/6818* (2013.01); *C12Q 1/6858* (2013.01); *C12Q 1/6881* (2013.01); *C12Q 1/6827* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

2012/0238455 A1   9/2012   Nakamura et al.

FOREIGN PATENT DOCUMENTS

| JP | 2009-261358 | 11/2009 | |
|---|---|---|---|
| JP | 2010-104360 | 5/2010 | |
| JP | 2012-187082 | 10/2012 | |
| WO | WO 9947706 A1 * | 9/1999 | ........... C12Q 1/6874 |
| WO | 2011/030159 | 3/2011 | |

OTHER PUBLICATIONS

Striano, P. et al. Expert Opinion on Investigational Drugs 18(12):1875 (2009).*
International Search Report dated Apr. 23, 2013 in International (PCT) Application No. PCT/JP2013/055285.
English translation of the International Preliminary Report on Patentability and Written Opinion dated Sep. 2, 2014.

(Continued)

*Primary Examiner* — Diana B Johannsen
(74) *Attorney, Agent, or Firm* — Wenderoth, Lind & Ponack, L.L.P.

(57) ABSTRACT

Provided is a method for detection of HLA-A*31:01 allele. One or more single nucleotide polymorphisms which characterize HLA-A*31:01 are analyzed and the presence or absence of HLA-A*31:01 is determined based on the result of the analysis.

8 Claims, 5 Drawing Sheets

(56) References Cited

OTHER PUBLICATIONS

WH Chung et al., "A Marker for Stevens-Johnson Syndrome", Nature, vol. 428, p. 486, Apr. 1, 2004.
T. Ozeki et al., "Genome-Wide Association Study Identifies HLA-A*3101 Allele as a Genetic Risk Factor for Carbamazepine-Induced Cutaneous Adverse Drug Reactions in Japanese Population", Human Molecular Genetics, vol. 20, No. 5, pp. 1034-1041, 2011.
M. McCormack et al., "HLA-A*3101 and Carbamazepine-Induced Hypersensitivity Reactions in Europeans", The New England Journal of Medicine, vol. 364, pp. 1134-1143, 2011.
SD Adams et al., "High Throughput HLA Sequence-Based Typing (SBT) Utilizing the ABI Prism 3700 DNA Analyzer", Tumori, vol. 87, No. 2, pp. S40-S43, Mar.-Apr. 2001, (Abstract only).
Y. Itoh et al., "High-Throughput DNA Typing of HLA-A, -B, -C and -DRB1 loci by a PCR-SSOP-Luminex Method in the Japanese Population", Immunogenetics, vol. 57, No. 10, pp. 717-729, Nov. 2005, (Abstract only).
R. Faner et al., "Real-Time PCR using Fluorescent Resonance Emission Transfer Probes for HLA-B Typing", Hum Immunol., vol. 67, Nos. 4-5, pp. 374-385, Apr.-May 2006, (Abstract only).
R. L. Erlich et al., "Next-Generation Sequencing for HLA Typing of Class I loci", BMC Genomics, vol. 12, No. 42, pp. 1-13, 2011.
C. Lind et al., "Next-Generation Sequencing: The Solution for High-Resolution, Unambiguous Human Leukocyte Antigen Typing", Hum Immunol., vol. 71, No. 10, pp. 1033-1042, 2010, (Abstract only).
C. Gabriel et al., "Rapid High-Throughput Human Leukocyte Antigen Typing by Massively Parallel Pyrosequencing for High-Resolution Allele Identification", Hum Immunol., vol. 70, No. 11, pp. 960-964, Nov. 2009, (Abstract only).
T. Muroshida, Riken News, 2011, No. 361, pp. 2-5 with partial English translation (p. 4, right column, line 4 from the bottom to p. 5, left column, line 10).
N. Hosono et al., "Development of New HLA-B*3505 Genotyping Method using Invader Assay", Pharmacogenetics and Genomics, vol. 20, pp. 630-633, 2010.
M. Aoki et al., "New Pharmacogenetic Test for Detecting an HLA-A*31:01 Allele using the InvaderPlus Assay", Pharmacogenetics and Genomics, vol. 22, pp. 441-446, Mar. 2012.
Extended European Search Report dated Sep. 15, 2015 in corresponding European patent application No. 13 75 4011.
Hiroko Ikeda et al., "HLA Class I markers in Japanese patients with carbamazepine-induced cutaneous adverse reactions", Epilepsia, vol. 51, No. 2, Feb. 1, 2010, pp. 297-0300, XP055211106.
Hiroyuki Niihara et al., "Simple and rapid detection of HLA-A*31:01 for prediction of carbamazepine-induced hypersensitivity using loop-mediated isothermal amplification method", Journal of Dermatological Science, vol. 74, No. 1, Apr. 1, 2014, pp. 88-92, XP028630325.

* cited by examiner (A) *HLA-A*31:01* assay by 7500 Fast PCR system (B) Agarose gel electrophoresis after reaction of InvaderPlus

METHOD FOR DETECTING HLA-A*31:01 ALLELE

TECHNICAL FIELD

The present invention relates to a method for detection of HLA-A*31:01 allele, a method for determination of the risk of drug eruption induced by an antiepileptic drug using the detection result obtained with the method for detection, and reagents used in the method for detection.

BACKGROUND ART

Drug eruption is a representative skin disorder caused by a drug (cutaneous adverse drug reaction; cADR) characterized by acute inflammatory reaction on skin and mucosa induced by a drug. Drug eruptions are dose-independent and unpredictable, and often life-threatening. Drug eruptions include those having a wide range of symptoms, from mild to severe, and examples of drug eruptions having severe symptoms include Stevens-Johnson syndrome (SJS), toxic epidermal necrolysis (TEN) and drug-induced hypersensitivity syndrome (DIHS), which are known as three major severe drug eruptions.

Almost all drugs reportedly have a risk to cause drug eruption, and above all, the antiepileptic drug carbamazepine (CBZ) is known to cause a variety of drug eruptions including SJS, TEN, and DIHS.

From previous studies, onset of drug eruption has been considered to involve T cell-mediated allergic reaction but its detailed mechanism of pathogenesis is unclear. Moreover, reactivation of human herpes virus 6 (HHV-6) is suggested to contribute to symptoms of DIHS such as fever and hepatitis but its mechanism of pathogenesis is obscure.

A study of CBZ using Taiwanese subjects has indicated that human leukocyte antigen (HLA)-B*1502 allele is strongly associated with SJS and TEN induced by CBZ (Non-Patent Document 1). However, allele frequencies of HLA loci are significantly different among different ethnic groups and HLA-B*1502 allele, for example, is found at a frequency of 8.6% in the Southeast Asian populations (Non-Patent Document 1), but only at a frequency of 0.1% in the Japanese and Caucasian populations (www.allelefrequencies.net). Therefore, HLA-B*1502 allele is not seen as a genetic factor useful for prediction of SJS and TEN induced by CBZ in the Japanese and Caucasian populations.

Recently, the relationship between HLA-A*31:01 allele and cADR induced by CBZ (CBZ-induced cADR) in Japanese subjects was revealed. That is, HLA-A*31:01 allele was present in 60.7% of the patients with CBZ-induced cADR, but only in 12.5% of the CBZ-tolerant subjects (odds ratio=10.8, P=$3.64 \times 10^{-15}$) (Non-Patent Document 2). Moreover, the relationship between HLA-A*31:01 allele and CBZ-induced cADR is reported also in the European populations (Non-Patent Document 3). Therefore, a pharmacogenetic test to identify subjects carrying HLA-A*31:01 allele will be useful to reduce the incidence of CBZ-induced cADR in both the Japanese and European populations.

Several HLA genotyping methods have been reported (Non-Patent Documents 4 to 6). Because the methods were labor-intensive and time-consuming, they had room for improvements. Moreover, a next-generation DNA sequencer is used recently to perform HLA genotyping (Non-Patent Documents 7 to 9), but it requires long reaction time and high cost and therefore the genotyping remains to be improved.

Moreover, detection of HLA-A*31:01 allele by combining a PCR assay and Invader assay is unknown.

PRIOR ART

Non-Patent Documents

[Non-Patent Document 1] Chung W H. et al. Nature. 2004 Apr. 1; 428(6982):486.
[Non-Patent Document 2] Ozeki T. et al. Hum Mol Genet. 2011; 20:1034-1041.
[Non-Patent Document 3] McCormack M. et al. N Engl J Med. 2011; 364:1134-1143.
[Non-Patent Document 4] Adams S D. et al. Tumori. 2001; 87:S40-43.
[Non-Patent Document 5] Itoh Y. et al. Hum Immunol. 2006; 67:374-385.
[Non-Patent Document 6] Faner R. et al. Hum Immunol. 2006; 67:374-385.
[Non-Patent Document 7] Erlich R L. et al. BMC Genomics. 2011; 12:42.
[Non-Patent Document 8] Lind C. et al. Hum Immunol. 2010; 71:1033-1042.
[Non-Patent Document 9] Gabriel C. et al. Hum Immunol. 2009; 70:960-964.

SUMMARY OF THE INVENTION

Problems to be Solved by the Invention

An object of the present invention is to provide a method for detection of HLA-A*31:01 allele.

Means for Solving the Problems

The inventors studied intensively to resolve the above-described problem and eventually found single nucleotide polymorphisms which enabled simple, quick and accurate detection of HLA-A*31:01 allele. Moreover, the inventors found that the combination of a PCR assay and Invader assay enabled simple, quick and accurate detection of HLA-A*31:01 allele. The inventors completed the present invention based on these findings.

That is, the present invention is as follows;
[1] A method for detection of HLA-A*31:01 comprising analyzing one or more single nucleotide polymorphisms which characterize HLA-A*31:01 and determining the presence or absence of HLA-A*31:01 based on the result of the analysis.
[2] The method according to [1], wherein the single nucleotide polymorphisms are analyzed by sequence-specific primer PCR assay in combination with InvaderPlus assay.
[3] The method according to [1] or [2], wherein one or more single nucleotide polymorphisms selected from the group consisting of rs1059449, rs41541222, rs1059471, rs1059457, and rs41562315 are analyzed.
[4] The method according to any one of [1] to [3], wherein at least rs41562315 is analyzed.
[5] A method of determining a risk of drug eruption induced by an antiepileptic drug comprising detecting HLA-A*31:01 by the method according to any one of [1] to [4], and determining the risk of drug eruption induced by the antiepileptic drug based on the result of the detection.
[6] The method according to [5], wherein the antiepileptic drug is carbamazepine.

[7] A sequence-specific primer set comprising (a) and (b) below:

(a) a first primer comprising a sequence with a length of 10 or more nucleotides in the nucleotide sequence of SEQ ID NO: 1 or the complementary sequence thereof, and comprising at the 3' end of the sequence a first single nucleotide polymorphism which characterizes HLA-A*31: 01;

(b) a second primer comprising a sequence with a length of 10 or more nucleotides in the nucleotide sequence of SEQ ID NO: 1 or the complementary sequence thereof, and comprising at the 3' end of the sequence a second single nucleotide polymorphism which characterizes HLA-A*31: 01, wherein the second primer is designed to be paired with the first primer for amplifying the region covering from the first single nucleotide polymorphism to the second single nucleotide polymorphism of HLA-A*31:01.

[8] The primer set according to [7], wherein the first single nucleotide polymorphism is rs41541222 or rs1059457, and the second single nucleotide polymorphism is rs41562315.

[9] A probe set comprising an Invader probe and an allelic probe, each of which targets a single nucleotide polymorphism which characterizes HLA-A*31:01 for an Invader.

[10] The probe set according to [9], wherein the single nucleotide polymorphism is rs1059471 or rs1059457.

[11] A reagent for detection of HLA-A*31:01 comprising the primer set according to [7] or [8] and the probe set according to [9] or [10], wherein the target single nucleotide polymorphism for the Invader is a single nucleotide polymorphism located between the first single nucleotide polymorphism and the second single nucleotide polymorphism.

EMBODIMENTS FOR CARRYING OUT THE INVENTION

Figure 1:
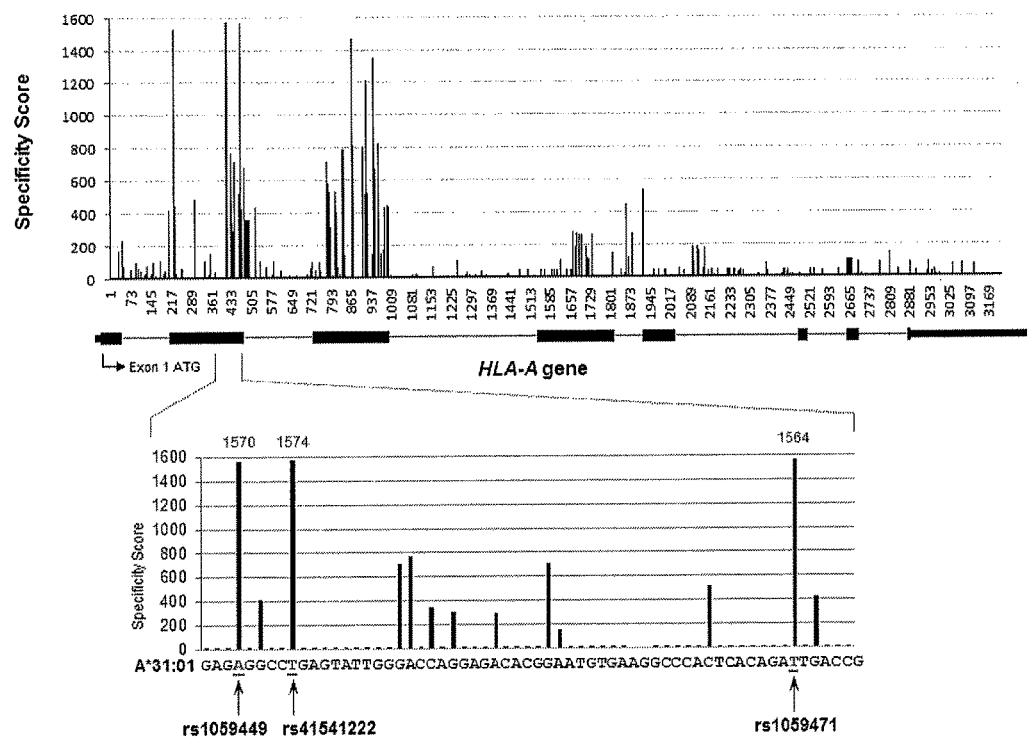
FIG. 1 shows the results of calculation of specificity score. Also, residues 364 through 425 of SEQ ID NO:1 are shown.

<1> The Method for Detection of HLA-A*31:01

The detection method of the present invention is a method for detection of HLA-A*31:01 comprising analyzing one or more single nucleotide polymorphisms (SNPs) which characterize HLA-A*31:01 and determining the presence or absence of HLA-A*31:01 based on the result of the analysis. The above-described "one or more" may represent one, two, three or more. In the present invention, "determination of the presence or absence of HLA-A*31:01" includes determination of the presence or absence of HLA-A*31:01 allele in a subject and determination of a degree of possibility that a subject carries HLA-A*31:01 allele. That is, in the detection method of the present invention, for example, it may be determined whether a subject carries HLA-A*31:01 allele or not. Moreover, in the detection method of the present invention, for example, a degree of possibility that a subject carries HLA-A*31:01 allele may be determined. In the present invention, "analysis" of SNPs has the same meaning as "assay" of SNPs.

HLA-A gene is a gene coding for the heavy chain of a HLA class I molecule. HLA-A gene is specifically represented by a region from 29,910,309 to 29,913,661 of GenBank Accession No. NC_000006.11. One thousand seven hundred twenty nine alleles of HLA-A gene have been registered in the IMGT/HLA Database (Oct. 13, 2011; version 3.6.0) and HLA-A*31:01 allele is one of them. The nucleotide sequence of HLA-A*31:01 allele is shown in SEQ ID NO: 1.

A SNP to be analyzed is not particularly restricted as long as it is a SNP which characterizes HLA-A*31:01 (HLA-A*31:01-discriminating SNP). A "SNP which characterizes HLA-A*31:01" means a SNP which can distinguish HLA-A*31:01 from one or more alleles selected from other HLA-A alleles.

The degree which characterizes HLA-A*31:01 will be described below introducing a concept of "specificity score". The difference between HLA-A*31:01 and each HLA-A allele of the known 1,729 HLA-A alleles is scored to each nucleotide starting from the translation initiation site and the sum of scores is called the "specificity score" at each nucleotide position. Specifically, first, the nucleotide at the translation initiation site of the reference HLA-A*31:01 allele is compared to the corresponding nucleotide of respective other HLA-A allele and +1 is added when the nucleotides are different. The nucleotide at the translation initiation site, i.e., the A in the start codon ATG, is identical in any of the HLA-A alleles and thus the specificity score at the translation initiation site is zero. This process is repeated sequentially for each nucleotide in a total of 3,216 bp (there are some differences in total number of nucleotides among alleles) and a specificity score is calculated using each nucleotide position in HLA-A*31:01 as a parameter. By definition, it is indicated that a nucleotide position where a higher specificity score is obtained is more specific to HLA-A*31:01, that is, the nucleotide position can distinguish HLA-A*31:01 allele from many other HLA-A alleles. Moreover, in other words, when the specificity score at a certain nucleotide position is X, the SNP at the nucleotide position is a SNP which can distinguish HLA-A*31:01 from X alleles out of the other HLA-A alleles.

The distribution of specificity score in HLA-A gene region is shown in FIG. 1. SNPs with a high specificity score exist especially in the latter half of exon 2 of HLA-A gene. For example, rs1059449, rs41541222, and rs1059471 locating in exon 2 have a specificity score of 1,500 or more, while rs1136659 and rs80321556 locating in exon 2 have a specificity score of 1,000 or more. Any of these SNPs can be preferably used for detection of HLA-A*31:01. Herein, an rs number represents a registration number in the dbSNP database of the National Center for Biotechnology Information (www.ncbi.nlm.nih.gov/projects/SNP/). In some SNPs, plural rs numbers are assigned to a single SNP. When a SNP is specified with an rs number in the present invention, the rs number alone may be assigned to the SNP or rs numbers other than the rs number may be simultaneously assigned to the SNP as long as the rs number is assigned to the SNP.

Moreover, a "SNP which characterizes HLA-A*31:01" are preferably selected considering the allele frequency of each HLA-A allele in the ethnic group to which a subject belongs. That is, a "SNP which characterizes HLA-A*31: 01" is preferably a SNP that can distinguish HLA-A*31:01 from other HLA-A alleles whose allele frequencies are high in the ethnic group to which a subject belongs. For example, a "SNP which characterizes HLA-A*31:01" is preferably a SNP that can distinguish HLA-A*31:01 from HLA-A alleles other than HLA-A*31:01, which exist at an allele frequency of more than 0.001% in the ethnic group to which a subject belongs.

Figure 2:
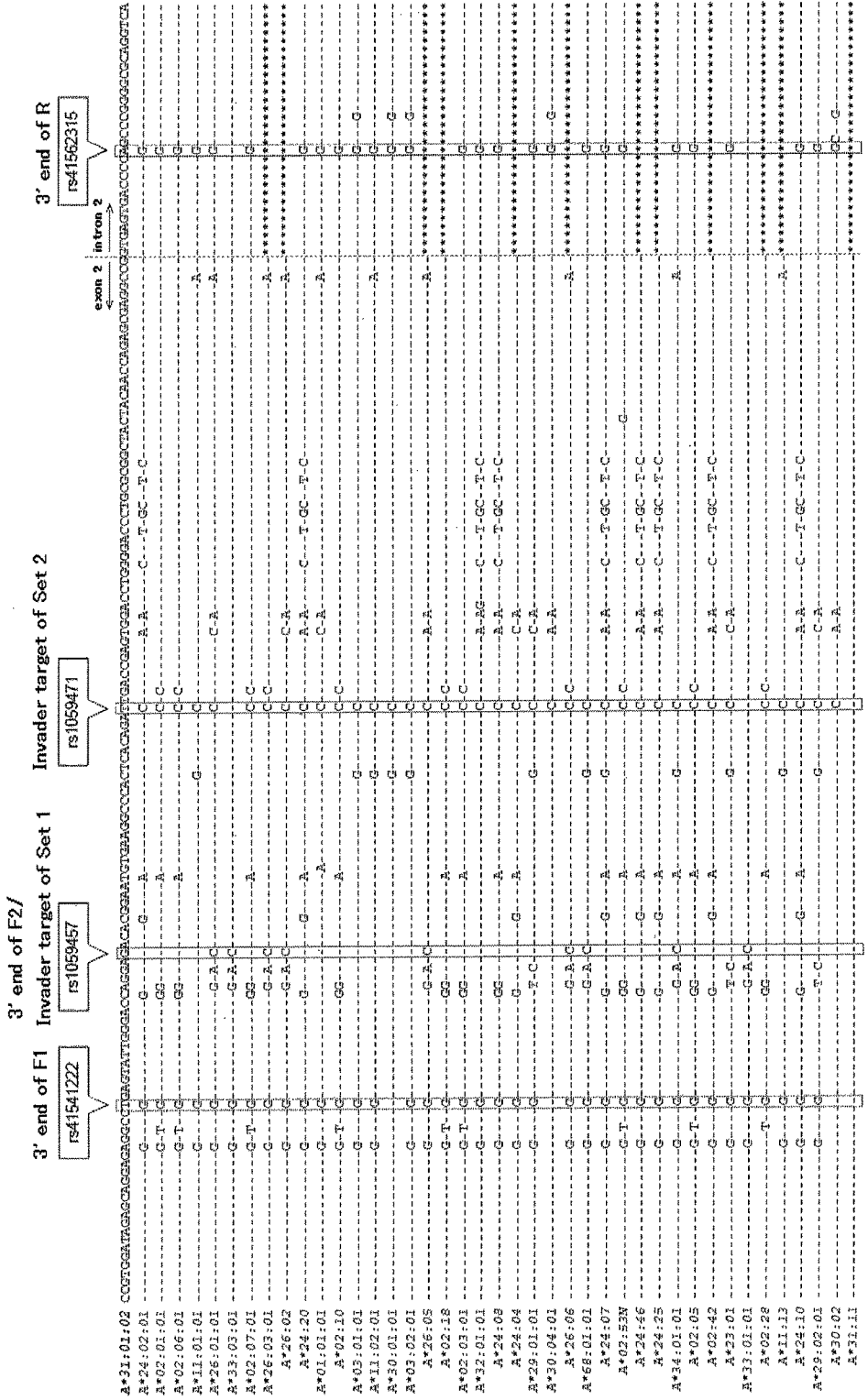
FIG. 2 shows the alignment of 42 HLA-A alleles with allele frequencies more than 0.001% in the Japanese population. An asterisk (*) in intron 2 means an unsequenced nucleotide. Nucleotides identical to those in HLA-A*31:01 are displayed as hyphen (-). The top line, A*31:01:02, shows residues 348 through 502 of SEQ ID NO:1.

For example, a total of 42 alleles including HLA-A*31:01 allele out of the known 1,729 HLA-A alleles have been reported by the Central Bone Marrow Data Center to exist in the Japanese population with an allele frequency of more than 0.001% (42 alleles described below in FIG. 2). Accordingly, when HLA-A*31:01 is detected in a Japanese subject, a "SNP which characterizes HLA-A*31:01" is preferably a SNP that can at least distinguish HLA-A*31:01 from one or more alleles selected from the other 41 HLA-A alleles. For example, the above-indicated rs1059449, rs41541222 and rs1059471 can be used preferably for detection of HLA-A*31:01 in, not particularly limited to, a Japanese subject.

In the present invention, a SNP with a high specificity score is preferable as a "SNP which characterizes HLA-A*31:01". As a SNP with a high specificity score, for example, a SNP selected from the top 10 SNPs is preferable, and a SNP selected from the top 5 SNPs is more preferable, in which the SNPs are sorted by their specificity scores in descending order. As a SNP with a high specificity score, for example, rs41541222, rs1059449, rs1059471, rs1136659, rs1059506, rs1059536, rs1059517, rs80321556, rs9260156, and rs1059509 are specifically represented. In the present invention, at least one SNP with a high specificity score is preferably analyzed, and at least 2 SNPs with high specificity scores are more preferably analyzed. A specificity score may be, for example, a score calculated for all HLA-A alleles or a score calculated for HLA-A alleles which exist at an allele frequency of more than 0.001% in the ethnic group to which a subject belongs.

Moreover, in the present invention, a "SNP which characterizes HLA-A*31:01" can be selected considering the above-mentioned specificity score and the homology between the nucleotide sequences of HLA-A*31:01 and each of other HLA-A alleles based on the sequence information of the known HLA-A gene. For example, a "SNP which characterizes HLA-A*31:01" is preferably a SNP which has a high specificity score and does not detect an HLA-A allele along with HLA-A*31:01, which HLA-A allele has both a high homology to HLA-A*31:01 and a high allele frequency in the population to which a subject belongs.

Moreover, when a "SNP which characterizes HLA-A*31:01" is analyzed by sequence-specific primer PCR, a SNP in a PCR amplified product of 200 bp or less, specifically, e.g., around 120 to 160 bp is preferable as such a SNP.

Moreover, a SNP in linkage disequilibrium with each of the above-described SNPs is represented as a "SNP which characterizes HLA-A*31:01". Herein, a "SNP in linkage disequilibrium with each of the above-described SNPs" refers to a SNP which satisfies a relationship of $r^2>0.5$, preferably a relationship of $r^2>0.8$, more preferably a relationship of $r^2>0.9$, especially preferably a relationship of $r^2=1$, with each of the above-described SNPs. A SNP in linkage disequilibrium with each of the above-described SNPs can be identified using, for example, the HapMap database (http://www.hapmap.org/index.html.ja) and the like. Moreover, a SNP in linkage disequilibrium with each of the above-described SNPs can be identified also by, for example, sequencing DNA samples collected from individuals (typically, around 20 to 40 individuals) with a DNA sequencer and searching SNPs in linkage disequilibrium. For example, rs41562315 is represented as a SNP in linkage disequilibrium with rs1059471.

In the present invention, for example, one or more SNPs selected at least from rs1059449, rs41541222, rs1059471, rs1059457, and rs41562315 may be analyzed. In respect to these five SNPs, a sequence of a total of 121 bp in length which comprises each of the SNP nucleotides and regions of 60 bp upstream and downstream thereof has been represented by each of SEQ ID NOs: 2 to 6. A polymorphism is located at the nucleotide position 61.

Moreover, in the present invention, for example, at least rs41562315 may be analyzed. Moreover, in the present invention, for example, at least rs41562315, rs41541222, and rs1059457 may be analyzed, or at least rs41562315, rs1059457, and rs1059471 may be analyzed.

In the present invention, analyzing each the above-described SNPs include analyzing a SNP corresponding to each of the above-described SNPs. A "SNP corresponding to each of the above-described SNPs" means a relevant SNP in HLA-A gene region. That is, "analyzing a SNP corresponding to each of the above-described SNPs" includes analyzing a relevant SNP in HLA-A gene region, even if the sequence of HLA-A gene varies at positions other than that of the SNP depending on different ethnic groups.

A sample to be used for SNP analysis is not particularly restricted as long as it is a sample containing chromosomal DNA. Examples thereof, for example, include a body fluid sample such as blood, urine or the like, cells of oral mucosa or the like, body hair such as hair or the like. These samples can be directly used for SNP analysis but it is preferred that chromosomal DNA is isolated from these samples by a conventional method and then used for the analysis.

SNP analysis can be performed with a standard genetic polymorphism analysis method. Examples thereof include, but not limited to, for example, sequence analysis, PCR, hybridization, Invader assay, and the like. In SNP analysis, for example, it may be determined which type of nucleotide is the nucleotide for each SNP to be analyzed, or whether or not the type of nucleotide for each SNP to be analyzed is identical to that in HLA-A*31:01. That is, for example, in cases where the type of nucleotide for a certain SNP in HLA-A*31:01 is A, in the analysis of a SNP to be analyzed, it may be determined which nucleotide among A, T, G and C is the nucleotide for the SNP, or, whether or not the nucleotide for the SNP is A. Moreover, in SNP analysis, either strand of double-stranded DNA may be analyzed.

Sequence analysis can be performed with a standard method. Specifically, a sequencing reaction is performed using a primer located tens of nucleotides 5' to a polymorphic nucleotide and the type of nucleotide at the corresponding position to the polymorphic nucleotide can be determined from the analysis result. A fragment comprising a SNP site is preferably amplified in advance by PCR and the like prior to the sequencing reaction.

Moreover, SNP analysis can be performed by examining the presence or absence of amplification by PCR. For example, a primer having a sequence corresponding to a region comprising each polymorphic nucleotide as well as the 3' end corresponding to the polymorphism is individually prepared. PCR is performed using each primer and the type of polymorphism can be determined based on the presence or absence of an amplified product. In the present invention, such a procedure is sometimes called "sequence-specific primer PCR (SSP-PCR) assay", in which a DNA fragment is amplified using a primer comprising a nucleotide corresponding to that for a SNP to be analyzed at its 3' end, only in cases where the nucleotide for the SNP to be analyzed is a specified nucleotide. Moreover, the presence or absence of amplification can be examined with LAMP method (the specification of Japanese Patent No. 3313358), NASBA method (Nucleic Acid Sequence-Based Amplification; the specification of Japanese Patent No. 2843586), ICAN method (Japanese Unexamined Patent Application Publication No. 2002-233379), and the like. Besides, a single chain amplification method may be employed.

Moreover, a DNA fragment comprising a SNP site is amplified and the type of polymorphism can be determined based on the difference in the electrophoresis mobility of the amplified product. An example of such a method includes PCR-SSCP (single-strand conformation polymorphism) method (Genomics. 1992 Jan. 1; 12(1): 139-146). Specifically, first, DNA comprising a SNP of interest is amplified and the amplified DNA is then dissociated into single-stranded DNAs. Subsequently, the dissociated single-stranded DNAs are separated on a non-denaturing gel and the type of polymorphism can be determined based on the difference in the mobility of the separated single-stranded DNAs on the gel.

Furthermore, in cases where a polymorphic nucleotide is included in a restriction enzyme recognition sequence, an analysis can be performed on the basis of the presence or absence of cleavage by a restriction enzyme (the RFLP method). In this case, a DNA sample is first digested with a restriction enzyme. The resulted DNA fragments are then separated and the type of polymorphism can be determined based on the size of the detected DNA fragments.

Moreover, the type of polymorphism can also be analyzed by examining the presence or absence of hybridization. That is, the type of nucleotide for a SNP can also be examined by preparing probes corresponding to respective nucleotides and examining which probe hybridizes to a sample.

Moreover, in the present invention, SNP analysis is preferably performed with sequence-specific primer PCR assay in combination with InvaderPlus assay. InvaderPlus assay is a procedure developed by Third Wave Technologies, Inc., in which PCR and Invader reaction are carried out sequentially in a single vessel. Invader assay is a procedure to detect a specific SNP using a cleavage enzyme (also referred to as "Cleavase") and a fluorescence resonance energy transfer (FRET) cassette and is broadly used in high throughput SNP genotyping. Invader assay is preferable because it can recognize a target SNP more specifically compared with the hybridization assay.

In this method, for example, sequence-specific primers (a sequence-specific forward primer and a sequence-specific reverse primer), an Invader probe, an allelic probe, a fluorescence-labeled FRET probe, Cleavase, dNTPs, Taq polymerase, and DNA to be analyzed are included in a reaction mixture to perform sequence-specific primer PCR followed by Invader reaction. Each sequence-specific primer is designed to have the nucleotide for a SNP to be analyzed at its 3' end and allow amplification of a DNA fragment during the process of sequence-specific primer PCR only in cases where the nucleotide for the SNP to be analyzed is a specified nucleotide. The allelic probe and the Invader probe are designed to hybridize to sequences located at both sides of the SNP targeted in the Invader reaction in the amplified fragment. The allelic probe comprises the nucleotide for the SNP to be analyzed at the 5' terminus of its hybridizing portion and a flap sequence extending 5' farther beyond the terminus. That is, the allelic probe is designed to comprise, sequentially in order from 5' end, the flap sequence, the SNP targeted in the Invader reaction, the sequence specific to the DNA to be analyzed. The Invader probe is designed such that the SNP site targeted in the Invader reaction locates at the 3' end of the probe and any type of nucleotide is accepted for the 3' end. A nucleotide in the allelic probe, which corresponds to the SNP targeted in the Invader reaction, is hybridized to the SNP nucleotide only in cases where the SNP in the amplified fragment is the specified nucleotide, and the nucleotide at the 3' end of the Invader probe (any type of nucleotide is accepted) further invades into the hybridized portion, and thus a triplex structure is formed at the SNP site. Then, Cleavase recognizes the triplex structure and cuts the allelic probe at the site between the nucleotide corresponding to the SNP and the above-described 5' terminus of the hybridizing portion, and the flap sequence comprising the SNP nucleotide at its 3' end is released. The released flap sequence hybridizes to the FRET probe and forms a similar triplex structure, followed by recognition of the triplex structure and release of a fluorescent label from the FRET probe by Cleavase and thereby obtained a fluorescent signal. That is, in cases where each of three target SNPs is a specified nucleotide, amplification of a DNA fragment and Invader reaction occur and then a fluorescent signal is obtained. The PCR and the subsequent Invader reaction can be performed according to standard methods. Moreover, for example, Cleavase VIII and Cleavase 2.0 can be used as a Cleavase.

In this method, for example, HLA-A*31:01 can be detected based on two SNPs targeted in the sequence-specific primer PCR and a SNP targeted in the Invader reaction. These SNPs can be appropriately selected considering various conditions such as, for example, the specificity score of each SNP, the size of each amplified fragment, the presence or absence of mismatch around each SNP, and the like.

Moreover, a case where HLA-A*31:01 is detected based on three target SNPs is indicated above, but the number of SNPs may be decreased or increased as long as a desired detection accuracy can be achieved. For example, sequence-specific primer PCR may be performed using a sequence-specific primer in combination with a generic primer which is not used for detection of a polymorphism, as long as desired detection accuracy can be achieved.

In the Invader reaction, utilizing plural FRET probes and allelic probes comprising flap sequences corresponding to the FRET probes allows simultaneous discrimination of multiple types of nucleotides at a certain SNP site and/or simultaneous detection which determines whether each of the nucleotides at plural SNP sites is a specified nucleotide or not.

As described above, it is determined which type of nucleotide is the nucleotide for a SNP to be analyzed, or whether or not the type of nucleotide for a SNP to be analyzed is identical to that of HLA-A*31:01. This allows determination of the presence or absence of HLA-A*31:01 allele in a subject or determination of a degree of possibility that a subject carries HLA-A*31:01 allele.

In the detection method of the present invention, when the types of nucleotides for all of the analyzed SNP(s) are identical to those of HLA-A*31:01, it can be determined that a subject carries HLA-A*31:01 allele, or that a subject may carry HLA-A*31:01 allele. In the detection method of the present invention, when a nucleotide specific to any of HLA-A alleles other than HLA-A*31:01 allele is detected along with that specific to HLA-A*31:01 allele, the presence or absence of HLA-A*31:01 allele in a subject or a degree of possibility that a subject carries HLA-A*31:01 allele can be determined considering the number of events where the nucleotide specific to the HLA-A allele other than HLA-A*31:01 allele is detected and the allele frequencies of the HLA-A allele other than HLA-A*31:01 allele in the ethnic group to which the subject belongs. In the detection method of the present invention, when a nucleotide specific to any of HLA-A alleles other than HLA-A*31:01 allele is detected along with that specific to HLA-A*31:01 allele, a process to distinguish HLA-A*31:01 allele from the HLA-A allele other than HLA-A*31:01 allele may be performed as necessary.

<2> a Method for Determination of the Risk of Drug Eruption Induced by an Antiepileptic Drug HLA-A*31:01 allele is known to be associated with cADR induced by carbamazepine (CBZ) (CBZ-induced cADR) (Non-Patent Documents 2 and 3). Accordingly, a risk of drug eruption induced by an antiepileptic drug such as CBZ can be determined based on a detection result for HLA-A*31:01 allele. That is, the present invention provides a method for determination of the risk of drug eruption induced by an antiepileptic drug (hereinafter, also referred to as the determination method of the present invention) comprising detecting HLA-A*31:01 allele with the detection method of the present invention and determining the risk of drug eruption induced by an antiepileptic drug based on the detection result. In the present invention, the phrase "risk of drug eruption" includes a risk of whether or not drug eruption is developed by administration of an antiepileptic drug, and a risk of whether or not drug eruption is deteriorated by administration of an antiepileptic drug. Accordingly, in the present invention, the term "test" includes a test to predict whether or not drug eruption is developed by administration of an antiepileptic drug, and a test to predict whether or not drug eruption is deteriorated by administration of an antiepileptic drug. In the determination method of the present invention, when a subject carries HLA-A*31:01 allele, the risk of drug eruption induced by an antiepileptic drug is determined to be high. Moreover, in the determination method of the present invention, when a subject does not carry HLA-A*31:01 allele, the risk of drug eruption induced by an antiepileptic drug is determined to be low.

Examples of drug eruption include, not particularly limited to, Stevens-Johnson syndrome (SJS), toxic epidermal necrolysis (TEN), drug-induced hypersensitivity syndrome (DIHS), erythema multiforme (EM), maculopapular eruption (MPE), erythema, erythroderma, fixed drug eruption, and the like.

As an antiepileptic drug, without particular limitation, an iminostilbene-based agent is preferable and carbamazepine (CBZ) is more preferable.

Examples of ethnic groups to which the determination method of the present invention can be applied include, but not limited to, for example, the Japanese population and the Caucasian populations.

In the determination method of the present invention, one or more SNPs selected from other SNPs associated with the risk of drug eruption induced by an antiepileptic drug may be collectively analyzed. Examples of such SNPs include, for example, SNPs located in the region 21.33 of the short arm of chromosome 6 (6p21.33 region) in human (Patent Document 2). Specifically, examples of SNPs located in the 6p21.33 region include, for example, rs1633021, rs2571375, rs1116221, rs2844796, rs1736971, rs1611133, rs2074475, rs7760172, rs2517673, rs2524005, rs12665039, and rs1362088, as well as SNPs in linkage disequilibrium with those SNPs (Patent Document 2).

<3> Detection Reagents of the Present Invention

The present invention also provides detection reagents such as primers and probes to detect HLA-A*31:01 allele.

Examples of the primers include primers usable in PCR to amplify DNA fragments comprising the above-described polymorphic sites or primers usable in sequencing of DNA fragments comprising the above-described polymorphic sites. Specifically, examples of the primers include a primer usable in amplification and/or sequencing of a region in the sequence of SEQ ID NO: 1 which comprises a SNP which characterizes HLA-A*31:01 and a primer usable in amplification and/or sequencing of a region in the sequence of any of SEQ ID NOs: 2 to 6 which comprises the 61st nucleotide in the nucleotide sequence. The length of such a primer is preferably 10 to 50 nucleotides, more preferably 15 to 35 nucleotides, and still further preferably 20 to 35 nucleotides.

Examples of the primers usable in PCR to amplify DNA fragments comprising the above-described polymorphic sites or the primers usable in sequencing of DNA fragments comprising the above-described polymorphic sites include a primer comprising a sequence of a region 5' to each of the above-described polymorphic nucleotides, preferably the region 30 to 100 nucleotides upstream therefrom, and a primer comprising a sequence complementary to a region 3' to each of the above-described polymorphic nucleotides, preferably the region 30 to 100 nucleotides downstream therefrom. Analysis of a polymorphism in an amplified DNA fragment can be performed with the above-indicated procedures such as, for example, Invader assay.

Examples of a primer used for assessment of a polymorphism on the basis of the presence or absence of amplification by PCR (also referred to as sequence-specific primer) include a primer which has a sequence comprising each of the above-described nucleotides and comprises each of the above-described nucleotides in its 3' side, a primer which has the complementary sequence of a sequence comprising each of the above-described nucleotides and comprises the complementary nucleotide of each of the above-described nucleotides in its 3' side, and the like. A primer used in pairs with a sequence-specific primer may be another sequence-specific primer or a generic primer which is not involved in detection of a polymorphism. In cases where a sequence-specific primer is used in combination with another sequence-specific primer, it is expected that HLA-A*31:01 can be detected more accurately.

Examples of sequence-specific primers, which amplify a DNA fragment in cases where HLA-A*31:01 allele exists, include, for example, a primer comprising a sequence with a length of 10 or more nucleotides and harboring a single nucleotide polymorphism at the 3' end of the primer, which sequence has at the 3' end of the sequence the single nucleotide polymorphism which characterizes HLA-A*31: 01 in a nucleotide sequence of SEQ ID NO: 1 or the complementary sequence thereof.

Moreover, a set of sequence-specific primers, which amplify a DNA fragment in cases where HLA-A*31:01 allele exists, includes, for example, a set comprising (A) and (B) below:

(A) a first primer comprising a sequence with a length of 10 or more nucleotides in the nucleotide sequence of SEQ ID NO: 1 or the complementary sequence thereof, and comprising at the 3' end of the sequence a first single nucleotide polymorphism which characterizes HLA-A*31: 01;

(B) a second primer comprising a sequence with a length of 10 or more nucleotides in the nucleotide sequence of SEQ ID NO: 1 or the complementary sequence thereof, and comprising at the 3' end of the sequence a second single nucleotide polymorphism which characterizes HLA-A*31:01, wherein the second primer is designed to be paired with the first primer for amplifying the region covering from the first single nucleotide polymorphism to the second single nucleotide polymorphism of HLA-A*31:01.

The above-described phrase "comprising the single nucleotide polymorphism at the 3' end of the primer" means that the above-described SNP site which characterizes HLA-A*31:01 in the above-described sequence with a length of 10 or more nucleotides is located at the 3' end of the primer. The above-described "a length of 10 or more nucleotides" may be, for example, a length of 10 or more nucleotides, a length of 15 or more nucleotides, or a length of 20 or more nucleotides. Moreover, the above-described "a length of 10 or more nucleotides" may be, for example, a length of 50 or less nucleotides, or a length of 35 or less nucleotides.

Each sequence-specific primer described above may comprise an arbitrary nucleotide sequence at its 5' region. Specifically, it means that, for example, when the aforementioned "a length of 10 or more nucleotides" in the first primer is a length of 15 nucleotides and the total length of the primer is 20 nucleotides, the 3' region of the primer, which consists of 15 nucleotides, comprises a sequence with 15 nucleotides comprising at the 3' end the first SNP in a nucleotide sequence of SEQ ID NO: 1 or the complementary sequence thereof, and the remaining part of the primer, i.e., 5 nucleotides of the 5' region, may comprise an arbitrary sequence.

The SNPs which characterize HLA-A*31:01 in the first primer and the second primer can be appropriately selected considering various conditions such as, for example, the specificity score of each SNP, the size of each amplified fragment, the presence or absence of mismatch around each SNP, and the like. Specifically, for example, the aforementioned first single nucleotide polymorphism may be rs41541222 or rs1059457, and the aforementioned second single nucleotide polymorphism may be rs41562315. Specifically, examples of a sequence-specific primer each corresponding to rs41541222, rs1059457, and rs41562315 include, for example, Primer F1 (CCGTGGATAGAGCAGGAGAGGCCT; SEQ ID NO: 7), Primer F2 (GAGAGGCCTGAGTATTGGGACCAGGAG; SEQ ID NO: 8), Primer R (TGACCTGCGCCCCGGGCT; SEQ ID NO: 9), respectively. Moreover, a sequence-specific primer may be a primer comprising a nucleotide sequence comprising, for example, 10 or more nucleotides from the 3' end of any of these primers, or a primer comprising a nucleotide sequence with an arbitrary nucleotide sequence added to the 5' end of the aforementioned nucleotide sequence.

Sequence-specific primers, which amplify a DNA fragment in cases where an allele other than HLA-A*31:01 exists, can be designed by changing the nucleotide at the 3' end of each primer to a nucleotide corresponding to the allele other than HLA-A*31:01.

Moreover, examples of the probe include a probe which comprises each of the above-described polymorphic sites and allows determination of the type of nucleotide at the polymorphic site by the presence or absence of hybridization. Specifically, examples of the probe include a probe with a length of 10 or more nucleotides which comprises a sequence harboring a SNP which characterizes HLA-A*31:01 in SEQ ID NO: 1 or the complementary sequence thereof, or a probe with a length of 10 or more nucleotides which comprises a sequence harboring the 61st nucleotide of the nucleotide sequence of any of SEQ ID NOs: 2 to 6 or the complementary sequence thereof. The length of the probe is preferably 15 to 35 nucleotides, and more preferably 20 to 35 nucleotides.

Moreover, examples of a probe set used for Invader assay include a set comprising an Invader probe and an allelic probe, each of which targets a single nucleotide polymorphism which characterizes HLA-A*31:01 for an Invader. Such a probe can be designed by employing a software program such as, for example, Universal Invader Design Software. An Invader probe/an allelic probe can be designed such that an Invader reaction progresses in cases where HLA-A*31:01 exists.

Such a set of an Invader probe/an allelic probe includes, for example, a set comprising (C) and (D) below:

(C) an Invader probe comprising a sequence with a length of 10 or more nucleotides in the nucleotide sequence of SEQ ID NO: 1 or the complementary sequence thereof, and comprising at the 3' end of the sequence a single nucleotide polymorphism which characterizes HLA-A*31:01, in which the nucleotide for the single nucleotide polymorphism is selected from A, T, G, and C;

(D) an allelic probe comprising, in 5' to 3' direction, a flap sequence and a sequence with a length of 10 or more nucleotides in the nucleotide sequence of SEQ ID NO: 1 or the complementary sequence thereof, and comprising at the 5' end of the sequence a single nucleotide polymorphism which characterizes HLA-A*31:01, which allelic probe is designed to be paired with the Invader probe to undergo an Invader reaction in cases where HLA-A*31:01 exists.

The above-described phrase "comprising the single nucleotide polymorphism at the 3' end of the probe, in which the nucleotide for the single nucleotide polymorphisms is selected from A, T, G, and C" means that the above-described SNP site which characterizes HLA-A*31:01 in the above-described sequence with a length of 10 or more nucleotides is located at the 3' end of the probe and any type of nucleotide may be accepted for the aforementioned nucleotide. The above-described "a length of 10 or more nucleotides" may be, for example, a length of 10 or more nucleotides, a length of 15 or more nucleotides, or a length of 20 or more nucleotides. Moreover, the above-described "a length of 10 or more nucleotides" may be, for example, a length of 50 or less nucleotides, or a length of 35 or less nucleotides.

The above-described Invader probe may comprise an arbitrary nucleotide sequence in its 5' region. Moreover, the above-described allelic probe may comprise an arbitrary nucleotide sequence in its 5' region and/or 3' region. It means, for example, when the aforementioned "a length of 10 or more nucleotides" in the Invader probe is 15 nucleotides and the total length of the probe is 20 nucleotides, the 3' region of the probe, which consists of 15 nucleotides, comprises a sequence with 15 nucleotides harboring at the 3' end the first SNP in a nucleotide sequence of SEQ ID NO: 1 or the complementary sequence thereof, and the remaining part of the probe, i.e., 5 nucleotides of the 5' region, may comprise an arbitrary sequence.

A SNP as an Invader target can be appropriately selected considering various conditions such as, for example, the specificity score of the SNP, the presence or absence of mismatch around the SNP, and the like. Specifically, a SNP as an Invader target may be, for example, rs1059457 or rs1059471. Specifically, examples of an Invader probe and an allelic probe, each of which utilizes rs1059457 as an Invader target, include, for example, Invader Probe 1 (CCTGAGTATTGGGACCAGGAT; SEQ ID NO: 10) and Allelic Probe 1 (FAM) (ATGACGTGGCAGACGACACGGAAT- GTGAAGG; SEQ ID NO: 11). Moreover, specifically, examples of an Invader probe and an allelic probe, each of which utilizes rs1059471 as an Invader target, include, for example, Invader Probe 2 (TGAAGGCCCACTCACA-GAA; SEQ ID NO: 12) and Allelic Probe 2 (FAM) (AT-GACGTGGCAGACTTGACCGAGTGGACC; SEQ ID NO: 13). Moreover, an Invader probe may be a probe comprising a nucleotide sequence comprising, for example, 10 or more nucleotides from the 3' end of any of these Invader probes, or a probe comprising a nucleotide sequence with an arbitrary nucleotide sequence added to the 5' end of the aforementioned nucleotide sequence. Moreover, an allelic probe may be a probe comprising a nucleotide sequence comprising, for example, a flap sequence and the following 10 or more nucleotides in a nucleotide sequence of any of these allelic probe, or a probe comprising a nucleotide sequence with an arbitrary nucleotide sequence added to the 5' end and/or the 3' end of the aforementioned nucleotide sequence.

The 5' sequence consisting of 14 nucleotides in each of the above-described Allelic Probe 1 (FAM) and Allelic Probe 2 (FAM) is a flap sequence labeled with FAM. Accordingly, when a label other than FAM is used in Invader assay, the flap sequence may be changed to a sequence relevant to the label other than FAM.

Detection reagents of the present invention may include a sequence-specific primer set and a probe set used for Invader assay. In cases where the primer set is used in combination with the probe set, a single nucleotide polymorphism as an Invader target may be selected from single nucleotide polymorphisms in the region between the aforementioned first single nucleotide polymorphism and the aforementioned second single nucleotide polymorphism.

Moreover, detection reagents of the present invention may include, in addition to these primers and/or probes, articles selected from a polymerase enzyme for PCR, buffers, reagents for hybridization, a FRET probe and Cleavase for Invader reaction, and the like.

EXAMPLES

The present invention will be described below more specifically by means of Example. However, the present invention is not restricted to these Examples. In the Example, "HLA-A*31:01:02" and "HLA-A*31:01" are identical each other.

In the Example, detection of HLA-A*31:01 allele was performed by combining sequence-specific primer PCR with InvaderPlus assay.

(1) Genomic DNA Samples

Three HapMap samples were employed as genomic DNA samples: a sample consisting of 90 unrelated individuals from Japanese and Han Chinese (JCH); a sample consisting of 90 Utah residents with ancestry from Northern and Western Europe (CEU); a sample consisting of 90 individuals from the Yoruba in Ibadan, Nigeria (YRI). All HapMap samples were purchased from Coriell Institute for Genomic Research. The HLA-A genotype data of the HapMap samples were obtained from Non-Patent Document 7 (Erlich R L. et al. BMC Genomics. 2011; 12:42.). Thirteen samples in JCH samples (14.4%) and four samples in CEU samples (4.4%) carried HLA-A*31:01 allele and any of YRI samples did not carry HLA-A*31:01 allele.

(2) Primer Design and Probe Design

Design of primers and probes was carried out by the following procedure with reference to a previous report (Hosono N. et al. Pharmacogenet Genomics. 2010; 20:630-633.). Moreover, Universal Invader Design Software was employed for probe sequence design. The information on HLA-A alleles was obtained from the IMGT/HLA Database (www.ebi.ac.uk/imgt/hla/).

A total 42 HLA-A alleles including HLA-A*31:01 allele out of the known 1,729 HLA-A alleles have been reported by the Central Bone Marrow Data Center to exist in the Japanese population with an allele frequency of more than 0.001% (n=223589). Thus, SNPs which characterize HLA-A*31:01 allele (HLA-A*31:01-discriminating SNPs) were searched by limiting the search to the 42 HLA-A alleles. As a result, several SNPs were found in exon 2 which were able to distinguish HLA-A*31:01 allele from other HLA-A alleles. The sequence alignment of the aforementioned 42 HLA-A alleles and their SNPs are shown in FIG. 2.

Rs41541222 at nucleotide position 372 was identified as the most discriminative SNP by comparing each HLA-A allele on the screen of the dbMHC Sequence Alignment Viewer. A "nucleotide position" is numbered in order with the position of the translation initiation site (i.e., the A in the start codon ATG) of HLA-A gene considered nucleotide number 1 and by counting the number of nucleotides within the same gene in the 5' to 3' direction. Moreover, the second most discriminative SNP was rs1059471 at nucleotide position 419, and the third most discriminative SNP was rs1059449 at nucleotide position 367.

Considering these SNP positions, Forward Primer F1, which comprises at the 3' end a nucleotide corresponding to the most discriminative rs41541222, was designed.

Next, the design of a reverse primer comprising at the 3' end a nucleotide corresponding to the second most discriminative rs1059471 was attempted. However, when the reverse primer was combined with the F1, appropriate Invader/allelic probes could not be designed presumably due to short amplicon size by employing Universal Invader Design Software. Therefore, another candidate SNP which characterizes HLA-A*31:01 was searched and rs41562315 (at nucleotide position 485) in intron 2, which position is close to exon 2, was found. Although the sequence information of intron regions was not fully supported, alignment comparison among 110 available genomic sequences suggested that rs41562315 was in absolute linkage disequilibrium with rs1059471. Thus, Reverse Primer R, which comprises at the 3' end a nucleotide corresponding to rs41562315, was designed.

Next, considering the number of nucleotide mismatches around an Invadertarget site, rs1059457 at nucleotide position 390 was selected as an Invadertarget site. Universal Invader Design Software was employed to design Invader Probe 1 and Allelic Probe 1 (FAM), each of which utilized rs1059457 as an Invader target site. Hereinafter, a primer/probe set consisting of Forward Primer F1, Reverse Primer R, Invader Probe 1, and Allelic Probe 1 (FAM) is referred to as Set 1.

Furthermore, a second primer/probe set (hereinafter, referred to as Set 2) was designed to support the HLA-typing result from Set 1. Reverse Primer R was common in Set 1 and Set 2. Forward Primer F2 of Set 2 was designed to comprise at the 3' end a nucleotide corresponding to rs1059457, which was the Invader target site of Set 1. Moreover, Invader Probe 2 and Allelic Probe 2 (FAM) were designed with the second most discriminative SNP, rs1059471, selected as an Invader target site.

Figure 3:
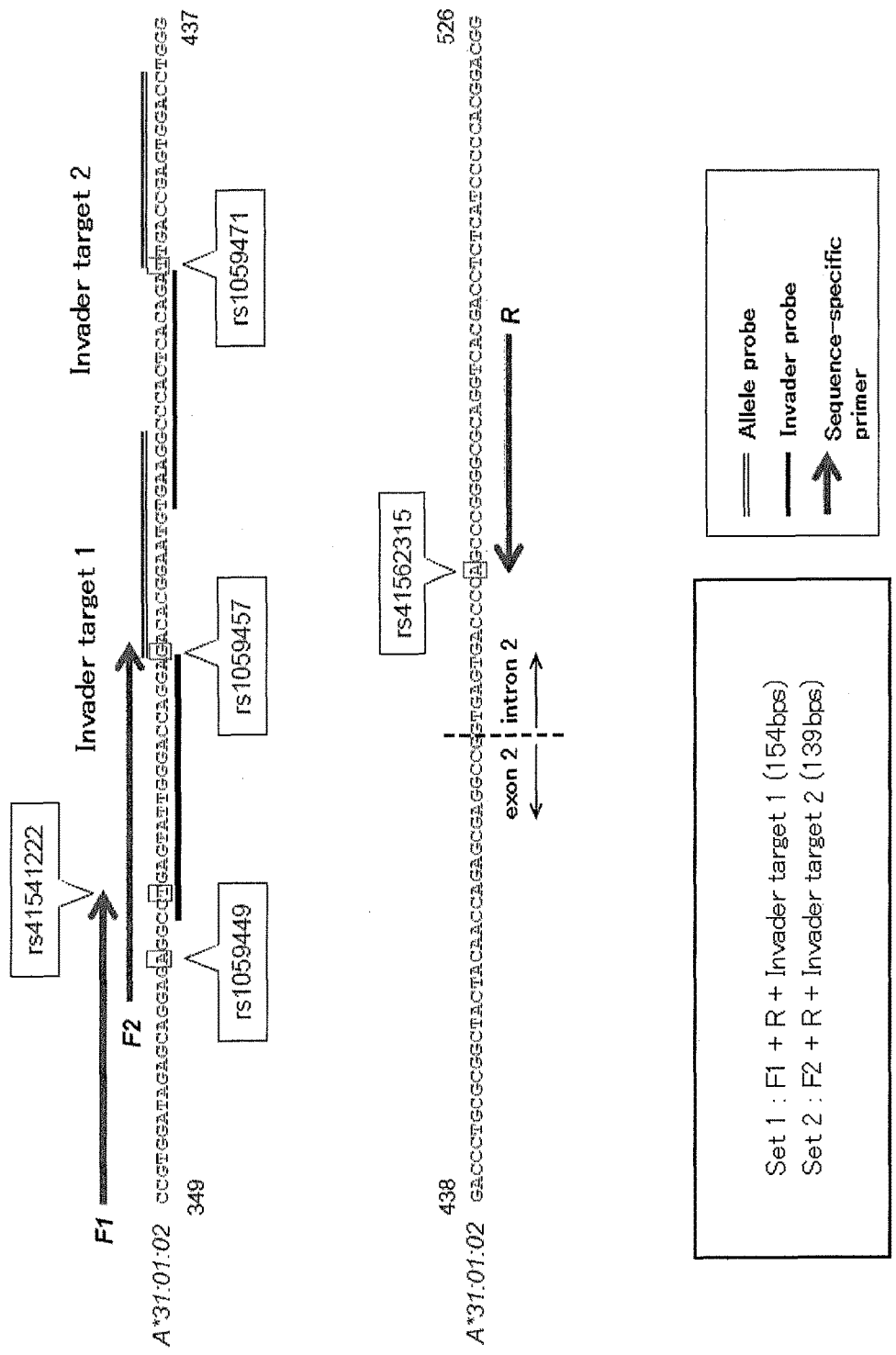
FIG. 3 shows the location of primers and probes of Set 1 and Set 2. Also, residues 349-437 of SEQ ID NO:1 are shown in the upper sequence and residues 438-526 of SEQ ID NO:1 are shown in the lower sequence.

The positions of primers and probes in each set are shown in FIG. 3, and the nucleotide sequences thereof are indicated in Table 1.

TABLE 1

| Primer and Probe | Sequence (5'-3') |
|---|---|
| Set 1 (amplicon size: 154 bp) | |
| Forward Primer F1 | CCGTGGATAGAGCAGGAGAGGCCT (SEQ ID NO: 7) |
| Reverse Primer R[a] | TGACCTGCGCCCCGGGCT (SEQ ID NO: 9) |
| Invader Probe 1 | CCTGAGTATTGGGACCAGGAT (SEQ ID NO: 10) |
| Allelic Probe 1(FAM)[b] | ATGACGTGGCAGACGACACGGAATGTGAAGG (SEQ ID NO: 11) |
| Set 2 (amplicon size: 139 bp) | |
| Forward Primer F2 | GAGAGGCCTGAGTATTGGGACCAGGAG (SEQ ID NO: 8) |
| Reverse Primer R[a] | TGACCTGCGCCCCGGGCT (SEQ ID NO: 9) |
| Invader Probe 2 | TGAAGGCCCACTCACAGAA (SEQ ID NO: 12) |
| Allelic Probe 2(FAM)[b] | ATGACGTGGCAGACTTGACCGAGTGGACC (SEQ ID NO: 13) |

[a] Reverse Primer R is common in Set 1 and Set 2.
[b] The underlined sequence represents a flap sequence labeled with FAM.

Both Set 1 and Set 2 are considered to detect HLA-A*31: 11, other than HLA-A*31:01, among SNPs existing in the Japanese population with an allele frequency of more than 0.001%. However, HLA-A*31:11 is quite rare in the Japanese population with an allele frequency of 0.002%, while the allele frequency of HLA-A*31:01 is 8.65% (that is, 4,325 times higher than the allele frequency of HLA-A*31: 11). Therefore, each primer/probe set designed above was assumed to be selective for HLA-A*31:01.

(3) InvaderPlus Assay

InvaderPlus assays were performed employing an ABI 7500 Fast real-time PCR system (Applied Biosystems, Foster City, Calif.) using 96-well plate. The reaction mixture contained 1×Signal Buffer, 1×FRET Mix (FRET22/FRET7), 60 ng of Cleavase VIII (all reagents were produced by Third Wave Technologies), 10 μM ROX (Sigma, MO, USA), 900 nM each of forward primer and reverse primer, 400 nM Invader probe, 800 nM allelic probe, 0.25 U Ex Taq HS DNA polymerase (Takara, Shiga, Japan), 400 μM dNTP mixture (Takara, Shiga, Japan), and 5 ng of genomic DNA in a total reaction volume of 10 μl. PCR was initiated at 95° C. for 20 seconds followed by 35 cycles at 98° C. for 3 seconds and 68° C. for 30 seconds. Following the PCR reaction, Invader reaction was performed at 99° C. for 30 seconds and at 63° C. for 10 minutes. The total reaction time was about 45 minutes. During the Invader reaction, fluorescence signals were measured every 30 seconds. Furthermore, PCR products after InvaderPlus assay were electrophoresed on a 2% agarose gel to evaluate the efficiency and the specificity of each primer set.

(4) Results

Figure 4:
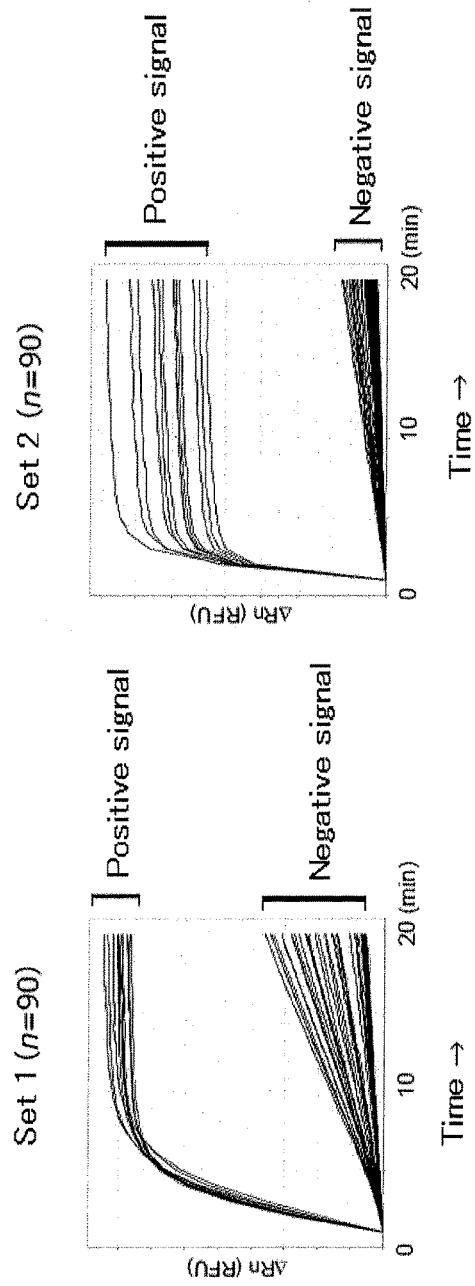
FIG. 4 is composed of drawings and pictures showing the result of an HLA-A*31:01 assay in JCH samples (n=90).
Figure 4:
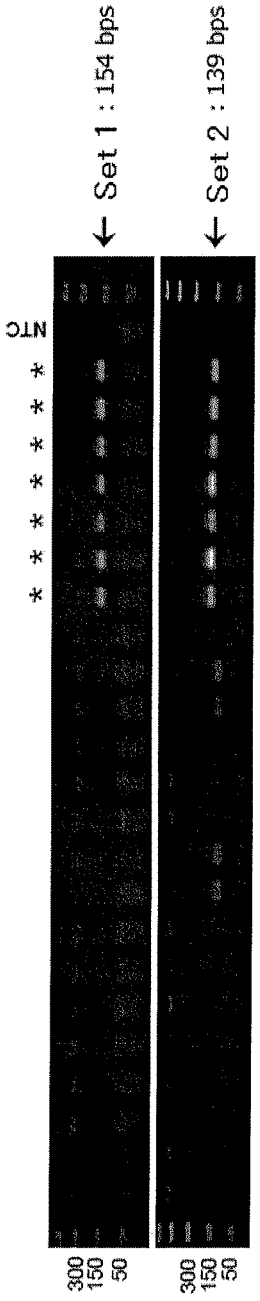

The result of an analysis using JCH samples (n=90) is presented in FIG. 4. When either primer/probe set was used, the primer/probe set was able to accurately distinguish HLA-A*31:01-positive samples (n=13) from HLA-A*31: 01-negative samples (n=77) without any false-positive signals. Moreover, according to the result of agarose gel electrophoresis, in each case where either primer set was used, the primer set was suggested to selectively amplify a targeted genomic region in the step of SSP-PCR.

Figure 5:
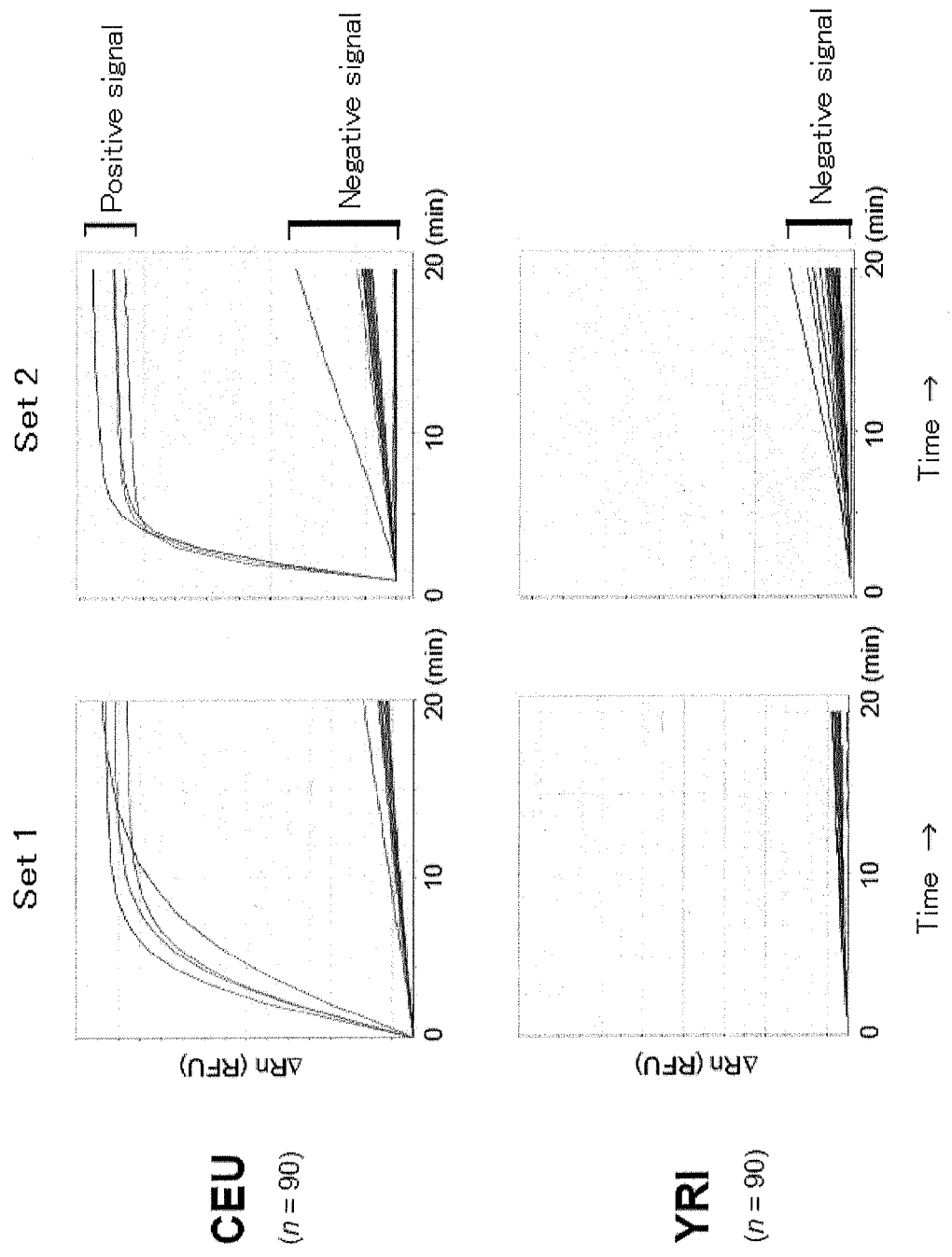
FIG. 5 shows the results of HLA-A*31:01 assay in CEU samples (n=90) and in YRI samples (n=90).

Moreover, the results of analyses using CEU samples (n=90) and YRI samples (n=90) are presented in FIG. 5. When either primer/probe set is used, the primer/probe set was able to accurately detect HLA-A*31:01-positive samples (n=4) in CEU samples. Moreover, in each case where either primer/probe set is used, no positive signal was detected in YRI samples where no HLA-A*31:01-positive sample exists, indicating no cross-reaction of the primer/probe set to HLA-A alleles other than HLA-A*31:01.

Accordingly, it was found that in each case where either primer/probe set, Set 1 or Set 2, was used, the primer/probe set was able to accurately detect the presence or absence of HLA-A*31:01 allele.

In silico analysis shows that 52 HLA-A alleles out of the known 1,729 HLA-A alleles may be detected in addition to HLA-A*31:01 by using either Set 1 or Set 2. According to the information registered in the Allele frequency net, the allele frequencies of 45 out of the 52 HLA-A alleles are zero and thus those alleles are considered not to influence the detection of HLA-A*31:01. On the other hand, the remaining 7 alleles are distributed among various ethnic groups at relatively low allele frequencies (0.006%-5.5%; Table 2). For example, the allele frequency of HLA-A*3102 allele is 1% or more in the Caucasian population. Accordingly, an analysis of the Caucasian population using Set 1 primer/probe set or Set 2 primer/probe set can detect HLA-A*3102 as well as HLA-A*31:01 at a frequency of 1% or more. To avoid false detection like this, for example, one can design an additional primer/probe set, which utilizes as a target a SNP that can distinguish HLA-A*31:01 from HLA-A*3102, and use the primer/probe set in combination with the primer/probe set of Set 1 or Set 2. Since FAM channel alone is used to detect HLA-A*31:01-derived signals using either Set 1 or Set 2, use of VIC fluorescence channel for the additional primer/probe set would allow simultaneous analysis. Examples of the SNP which can distinguish HLA-A*31:01 from HLA-A*3102, include, for example, rs1059460.

TABLE 2

| | Reported Population | Ethnic Origin | Allele Frequency | Sample Size |
|---|---|---|---|---|
| A*31:02 | Azores Santa Maria and San Miguel | Caucasoid | 0.013 | 43 |
| | Georgia Svaneti Region Svan | Caucasoid | 0.013 | 80 |
| | Azores Terceira Island | Caucasoid | 0.004 | 130 |
| | Mongolia Buryat | Oriental | 0.004 | 141 |
| | USA Hispanic population 2 | Hispanic | 0.002 | 2352 |
| | USA Mexican American Mestizo | Mestizo | 0.002 | 553 |
| | China Beijing Shijiazhuang Taipei Han | Oriental | 0.001 | 618 |
| | Germany population 6 | Caucasoid | 0.00006 | 8862 |
| A*31:03 | Jordan Amman | Arab | 0.055 | 146 |
| | Kenya Luo | Black | 0.008 | 265 |
| | Zimbabwe Harare Shona | Black | 0.007 | 230 |
| | Kenya Nandi | Black | 0.006 | 240 |
| | China Inner Mongolia | Oriental | 0.005 | 102 |

TABLE 2-continued

| Reported Population | Ethnic Origin | Allele Frequency | Sample Size |
|---|---|---|---|
| Region | | | |
| Spain Andalusia | Caucasoid | 0.005 | 99 |
| A*31:04 Kenya | Black | 0.024 | 144 |
| Sudan (Mixed) | Mixed (South Africa) | 0.01 | 200 |
| Uganda Kampala population 2 | Black | 0.009 | 175 |
| Uganda Kampala | Black | 0.003 | 161 |
| Saudi Arabia Guraiat and Hail | Arab | 0.002 | 213 |
| China Beijing Shijiazhuang Taipei Han | Oriental | 0.001 | 618 |
| USA African American population 4 | Black | 0.00021 | 2411 |
| A*31:05 Mongolia Buryat | Oriental | 0.004 | 141 |
| A*31:06 China Beijing Shijiazhuang Taipei Han | Oriental | 0.002 | 618 |
| A*31:09 Peru Titikaka Lake Uro | Amerindian | 0.005 | 105 |
| USA Mexican American Mestizo | Mestizo | 0.001 | 553 |
| USA Hispanic population 2 | Hispanic | 0.00025 | 1999 |
| A*31:12 USA Asian population 2 | Asian | 0.00028 | 1772 |

Moreover, as mentioned above, in cases where either Set 1 or Set 2 is used, a rare allele existing in the Japanese population HLA-A*31:11 cannot be distinguished from HLA-A*31:01. The relationship between HLA-A*31:11 and the risk of drug eruption is unknown. However, as is the case described above, HLA-A*31:11 can be distinguished from HLA-A*31:01 by combined use of an additional primer/probe set. Examples of a SNP which can distinguish HLA-A*31:01 from HLA-A*31:11 include, for example, a SNP (no rs number assigned) locating at nucleotide position 936 in exon 3.

Furthermore, since HLA class I alleles were known to be highly homologous to each other, the possibility of co-amplification from other genomic HLA regions was examined by the following procedure. A region which had relatively high homology (maximally 87.6%) to a region amplified by Set 1 primer set or Set 2 primer set was identified in each of HLA-L region, HLA-B region and HLA-C region by searching at UCSC Blat Search (genome.ucsc.edu/index.html). Thus, based on the data registered in the IMGT/HLA Database version 3.6.0, whether or not Set 1 primer set or Set 2 primer set would amplify those regions was examined by using the dbMHC Sequence Alignment Viewer. Because the sequence information of intron regions was incomplete, the presence or absence of mismatch at the 3' end of Reverse Primer R was ignored. The examination resulted in identification of two alleles out of 2,329 HLA-B alleles (HLA-B*40:22N and HLA-B*40:134), no alleles out of 1,291 HLA-C alleles and no alleles out of 5 HLA-L alleles, which alleles had potential to be amplified. The nucleotide of each Invader target site for the above-described two HLA-B alleles is identical to that for HLA-A*31:01 and thus Set 1 primer/probe set or Set 2 primer/probe set cannot distinguish those two alleles from HLA-A*31:01. However, according to the information registered in the Allele frequency net, the allele frequencies of these two HLA-B alleles are zero and therefore Set 1 primer/probe set or Set 2 primer/probe set is less likely to amplify other genomic HLA regions.

INDUSTRIAL APPLICABILITY

In accordance with the present invention, HLA-A*31:01 allele can be detected. In particular, in one aspect of the present invention, HLA-A*31:01 allele can be detected simply, quickly, and accurately by determining a specific SNP(s). Moreover, in particular, in one aspect of the present invention, HLA-A*31:01 allele can be detected simply, quickly, and accurately by combining a PCR assay and Invader assay. Moreover, the risk of drug eruption induced by an antiepileptic drug, which is associated with HLA-A*31:01 allele, can be predicted using the results of detection of HLA-A*31:01 allele. Therefore, the present invention is effective in determination of whether or not an antiepileptic drug can be applied, and thus contributes to antiepileptic drug therapy.

The invention claimed is:

1. A method for detection of HLA-A*31:01 comprising analyzing one or more single nucleotide polymorphisms which characterize HLA-A*31:01 with a reagent for detection of HLA-A*31:01 and determining the presence or absence of HLA-A*31:01 based on the result of the analysis,
wherein the reagent for detection of HLA-A*31:01 comprising:
a sequence-specific primer set comprising a first primer which comprises the nucleotide sequence of SEQ ID NO:7 or SEQ ID NO:8 and a second primer which comprises the nucleotide sequence of SEQ ID NO:9: and
a probe set comprising:
an Invader probe comprising a sequence consisting of at least 10 contiguous nucleotides in the nucleotide sequence of SEQ ID NO:1 or the complementary sequence thereof wherein a single nucleotide polymorphism selected from the group consisting of rs1059471 and rs1059457 is located at the 3' end of said sequence consisting of at least 10 contiguous nucleotides in the nucleotide sequence of SEQ ID NO:1 or the complementary sequence thereof; and
an allelic probe comprising, in 5' to 3' direction, a flap sequence and a sequence consisting of at least 10 contiguous nucleotides in the nucleotide sequence of SEQ ID NO:1 or the complementary sequence thereof wherein the single nucleotide polymorphism selected from the group consisting of rs1059471 and rs1059457 is located at the 5' end of said sequence consisting of at least 10 contiguous nucleotides in the nucleotide sequence of SEQ ID NO:1 or the complementary sequence thereof, wherein the allelic probe is oriented with the Invader probe to be a probe pair for an Invader reaction.

2. The method according to claim 1, wherein the single nucleotide polymorphisms are analyzed by sequence-specific primer PCR assay in combination with InvaderPlus assay.

3. The method according to claim 1, wherein one or more single nucleotide polymorphisms selected from the group consisting of rs1059449, rs41541222, rs1059471, rs1059457, and rs41562315 are analyzed.

4. The method according to claim 1, wherein at least rs41562315 is analyzed.

5. A method of determining a risk of drug eruption induced by an antiepileptic drug comprising detecting HLA-A*31:01 by the method according to claim 1, and determining the risk of drug eruption induced by the antiepileptic drug based on the result of the detection, wherein the antiepileptic drug is carbamazepine.

6. A reagent for detection of HLA-A*31:01 comprising:
a sequence-specific primer set comprising a first primer which comprises the nucleotide sequence of SEQ ID NO:7 or SEQ ID NO:8 and a second primer which comprises the nucleotide sequence of SEQ ID NO:9: and
a probe set comprising:
an Invader probe comprising a sequence consisting of at least 10 contiguous nucleotides in the nucleotide sequence of SEQ ID NO:1 or the complementary sequence thereof wherein a single nucleotide polymorphism selected from the group consisting of rs1059471 and rs1059457 is located at the 3' end of said sequence consisting of at least 10 contiguous nucleotides in the nucleotide sequence of SEQ ID NO:1 or the complementary sequence thereof; and
an allelic probe comprising, in 5' to 3' direction, a flap sequence and a sequence consisting of at least 10 contiguous nucleotides in the nucleotide sequence of SEQ ID NO:1 or the complementary sequence thereof wherein the single nucleotide polymorphism selected from the group consisting of rs1059471 and rs1059457 is located at the 5' end of said sequence consisting of at least 10 contiguous nucleotides in the nucleotide sequence of SEQ ID NO:1 or the complementary sequence thereof, wherein the allelic probe is oriented with the Invader probe to be a probe pair for an Invader reaction.

7. The reagent according to claim 6, wherein the Invader probe comprises the nucleotide sequence of SEQ ID NO: 10 and the allelic probe comprises the nucleotide sequence of SEQ ID NO: 11.

8. The reagent according to claim 6, wherein the Invader probe comprises the nucleotide sequence of SEQ ID NO: 12 and the allelic probe comprises the nucleotide sequence of SEQ ID NO: 13.

* * * * *

SEQUENCE LISTING

<160> NUMBER OF SEQ ID NOS: 13

<210> SEQ ID NO 1
<211> LENGTH: 3216
<212> TYPE: DNA
<213> ORGANISM: Homo sapiens

<400> SEQUENCE: 1

```
atggccgtca tggcgcccg  aaccctcctc ctgctactct tgggggccct ggccctgacc      60
cagacctggg cgggtgagtg cggggtcgtg gggaaaccgc ctctgcgggg agaagcaagg     120
ggcccgcccg gcggggggcgc aggacccggg tagccgcgcc gggaggaggg tcgggcggat     180
ctcagccact cctcgccccc aggctcccac tccatgaggt atttcaccac atccgtgtcc     240
cggcccggcc gcggggagcc ccgcttcatc gccgtgggct acgtggacga cacgcagttc     300
gtgcggttcg acagcgacgc cgcgagccag aggatggagc gcgggcgcc  gtggatagag     360 caggagaggc ctgagtattg ggaccaggag acacggaatg tgaaggccca ctcacagatt     420
gaccgagtgg acctggggac cctgcgcggc tactacaacc agagcgaggc cggtgagtga     480
ccccagcccg gggcgcaggt cacgacctct catcccccac ggacgggcca ggtcacccac     540
```

-continued

```
agtctccggg tccgagatcc accccgaagc cgcgggaccc cgagacccct gccccgggag      600
aggcccaggc gcctttaccc ggtttcattt tcagtttagg ccaaaaatcc ccccgggttg      660
gtcggggccg gacggggctc gggggactgg gctgaccgtg gggtcgggggc caggttctca    720 caccatccag atgatgtatg gctgcgacgt ggggtcggac gggcgcttcc tccgcgggta     780
ccagcaggac gcctacgacg gcaaggatta catcgccttg aacgaggacc tgcgctcttg     840
gaccgcggcg gacatggcgg ctcagatcac ccagcgcaag tgggaggcgg cccgtgtggc     900
ggagcagttg agagcctacc tggagggcac gtgcgtggag tggctccgca gatacctgga    960
gaacgggaag gagacgctgc agcgcacggg taccaggggc cacggggcgc ctccctgatc     1020
gcctgtagat ctcccgggct ggcctccac aaggagggga gacaattggg accaacacta     1080
gaatatcacc ctccctctgg tcctgaggga gggaatcct cctgggtttc cagatcctgt      1140
accagagagt gactctgagg ttccgccctg ctctgtgaca caattaaggg ataaaatctc     1200
tgaaggaatg acgggaagac gatccctcga atactgatga gtggttccct ttgacacaca    1260
ccggcagcag ccttgggccc gtgactttc ctctcaggcc ttgttctctg cttcacactc      1320
aatgtgtgtg ggggtctgag tccagcactt ctgagtccct cagcctccac tcaggtcagg    1380
accagaagtc gctgttccct cttcagggac tagaatttc cacggaatag gagattatcc     1440
caggtgcctg tgtccaggct ggtgtctggg ttctgtgctc ccttccccat cccaggtgtc     1500
ctgtccattc tcaagatagc cacatgtgtg ctggaggagt gtcccattac agatgcaaaa    1560
tgcctgaatg ttctgactct tcctgacaga ccccccaag acgcatatga ctcaccacgc     1620
tgtctctgac catgaggcca ccctgaggtg ctgggccctg agcttctacc ctgcggagat    1680
cacactgacc tggcagcggg atggggagga ccagacccag gacacggagc tcgtggagac   1740
caggcctgca ggggatggaa ccttccagaa gtgggcgtct gtggtggtgc cttctggaca    1800
ggagcagaga tacacctgcc atgtgcagca tgagggtctc cccaagcccc tcaccctgag    1860
atggggtaag gagggagatg ggggtgtcat gtctttagg gaaagcagga gcctctctga     1920
cctttagcag ggtcagggcc cctcaccttc ccctctttc ccagagccgt ctttcccagcc    1980 caccatcccc atcgtgggca tcattgctgg cctagttctc tttggagctg tgttcgctgg    2040
agctgtggtc gctgctgtga ggtggaggag gaagagctca ggtggggtga aggggtgaag   2100
ggtgggtctg agatttcttg tctcactgag ggttccaaga cccaggtaga agtgtgccct    2160
gcctcgttac tgggaagcac catccacaat tatgggccta cccagcctgg gccctgtgtg   2220
ccagcactta ctcttttgta aagcacctgt taaaatgaag acagattta tcaccttgat    2280 tatggcggtg atgggacctg atcccagcag tcacaagtca caggggaagg tccctgagga   2340
ccttcaggag ggcggttggt ccaggaccca cacctgcttt cttcatgttt cctgatcccg   2400
ccctgggtct gcagtcacac atttctggaa acttctctga ggtccaagac ttggaggttc   2460
ctctaggacc ttaaggccct ggctcctttc tggtatctca caggacattt tcttcccaca    2520
gatagaaaag gagggagcta ctctcaggct gcaagtaagt atgaaggagg atgatccaag    2580
aaatcactgg gatattgtgt ttgggagccc gtgggggagc tcacccaccc cacaattcct    2640
cctctagcca catcttctgt gggatctgac caggttctgt ttttgtccta ccccaggcag   2700
tgacagtgcc cagggctctg atatgtctct cacagcttgt aaaggtgaga gcctggaggg   2760
cctgatgtgt gttgggtgtt gggcggaaca gtggacgcag ctgtgctatg ggtttctttt   2820
gcattggatg tattgagcat gcgatgggct gtttaaagtg tgactcctca ctgtgacaga   2880
```

-continued

```
tacgaatttg ttcatgaata ttttttttcta tagtgtgaga cagctgcctt gtgtgggact    2940
gagaggcaag atttgttcct gcccttccct ttgtgacttg aagtaccctg actttgtttc    3000
tgcaaaggca cctgcatgtg tctgtgttct tgtaggcata atgtgaggag gtggggagac    3060 cacccccaccc ccatgtccac catgaccctc ttcccacgct gacctgtgct ccctccccaa    3120
tcatctttcc tgttccagag aggtggggct gaggtgtctc catctctgcc tcaacttcat    3180
ggtgcactga gctgtaactt cttccttccc tattaa                               3216

<210> SEQ ID NO 2
<211> LENGTH: 121
<212> TYPE: DNA
<213> ORGANISM: Homo sapiens

<400> SEQUENCE: 2
ttcgacagcg acgccgcgag ccagaggatg gagccgcggg cgccgtggat agagcaggag     60
rggccggagt attgggacca ggagacacgg aatgtgaagg cccagtcaca gactgaccga   120
g                                                                    121

<210> SEQ ID NO 3
<211> LENGTH: 121
<212> TYPE: DNA
<213> ORGANISM: Homo sapiens

<400> SEQUENCE: 3
cagcgacgcc gcgagccaga ggatggagcc gcggcgccg tggatagagc aggaggggcc     60
dgagtattgg gaccaggaga cacggaatgt gaaggcccag tcacagactg accgagtgga   120
c                                                                    121

<210> SEQ ID NO 4
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t

<400> SEQUENCE: 4
agcaggaggg gccggagtat tgggaccagg agacacggaa tgtgaaggcc cagtcacaga     60
ntgaccgagt ggacctgggg accctgcgcg gctactacaa ccagagcgag gccggtgagt   120
g                                                                    121

<210> SEQ ID NO 5
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t

<400> SEQUENCE: 5
gaggatggag ccgcgggcgc cgtggataga gcaggagggg ccggagtatt gggaccagga     60
nacacggaat gtgaaggccc agtcacagac tgaccgagtg gacctgggga ccctgcgcgg   120
c                                                                    121

<210> SEQ ID NO 6
<211> LENGTH: 121
```

```
<212> TYPE: DNA
<213> ORGANISM: Homo sapiens

<400> SEQUENCE: 6
gagtggacct ggggaccctg cgcggctact acaaccagag cgaggccggt gagtgacccc    60
rgccgggggc gcaggtcagg acccctcatc ccccacggac gggccaggtc gcccacagtc   120
t                                                                  121

<210> SEQ ID NO 7
<211> LENGTH: 24
<212> TYPE: DNA
<213> ORGANISM: Artificial Sequence
<220> FEATURE:
<223> OTHER INFORMATION: primer F1

<400> SEQUENCE: 7
ccgtggatag agcaggagag gcct                                           24

<210> SEQ ID NO 8
<211> LENGTH: 27
<212> TYPE: DNA
<213> ORGANISM: Artificial Sequence
<220> FEATURE:
<223> OTHER INFORMATION: primer F2

<400> SEQUENCE: 8
gagaggcctg agtattggga ccaggag                                        27

<210> SEQ ID NO 9
<211> LENGTH: 18
<212> TYPE: DNA
<213> ORGANISM: Artificial Sequence
<220> FEATURE:
<223> OTHER INFORMATION: primer R

<400> SEQUENCE: 9
tgacctgcgc cccgggct                                                  18

<210> SEQ ID NO 10
<211> LENGTH: 21
<212> TYPE: DNA
<213> ORGANISM: Artificial Sequence
<220> FEATURE:
<223> OTHER INFORMATION: invader probe 1

<400> SEQUENCE: 10
cctgagtatt gggaccagga t                                              21

<210> SEQ ID NO 11
<211> LENGTH: 31
<212> TYPE: DNA
<213> ORGANISM: Artificial Sequence
<220> FEATURE:
<223> OTHER INFORMATION: allele probe 1

<400> SEQUENCE: 11
atgacgtggc agacgacacg gaatgtgaag g                                   31

<210> SEQ ID NO 12
<211> LENGTH: 19
<212> TYPE: DNA
<213> ORGANISM: Artificial Sequence
<220> FEATURE:
<223> OTHER INFORMATION: invader probe 2
```

```
<400> SEQUENCE: 12
tgaaggccca ctcacagaa                                              19

<210> SEQ ID NO 13
<211> LENGTH: 29
<212> TYPE: DNA
<213> ORGANISM: Artificial Sequence
<220> FEATURE:
<223> OTHER INFORMATION: allele probe 2

<400> SEQUENCE: 13
atgacgtggc agacttgacc gagtggacc                                   29
```